(12) United States Patent
Gow et al.

(10) Patent No.: US 7,294,353 B2
(45) Date of Patent: Nov. 13, 2007

(54) **METHODS AND COMPOSITIONS COMPRISING *ILEX***

(75) Inventors: Robert T. Gow, Naples, FL (US);
George W. Sypert, Naples, FL (US);
John Pierce, Thousand Oaks, CA (US);
Dan Li, Naples, FL (US); Xun Yan,
Naples, FL (US); Rodger M. Marentis,
Macungie, PA (US)

(73) Assignee: HerbalScience, LLC, Naples, FL (US)

( * ) Notice: Subject to any disclaimer, the term of this patent is extended or adjusted under 35 U.S.C. 154(b) by 0 days.

(21) Appl. No.: 10/970,017

(22) Filed: Oct. 21, 2004
(Under 37 CFR 1.47)

(65) Prior Publication Data

US 2005/0089591 A1    Apr. 28, 2005

Related U.S. Application Data

(60) Provisional application No. 60/514,187, filed on Oct. 24, 2003.

(51) Int. Cl.
*A61K 36/00*    (2006.01)
(52) U.S. Cl. .................................... 424/725
(58) Field of Classification Search .................. None
See application file for complete search history.

(56) References Cited

U.S. PATENT DOCUMENTS

| | | | |
|---|---|---|---|
| 2,115,411 A | 4/1938 | Cortez | |
| 4,154,823 A | 5/1979 | Schutt | |
| 4,248,861 A | 2/1981 | Schutt | |
| 5,178,735 A | 1/1993 | Manabe et al. | |
| 5,234,947 A | 8/1993 | Cherksey | |
| 5,273,754 A | 12/1993 | Mann | |
| 5,296,224 A | 3/1994 | Schwabe | |
| 5,380,826 A | 1/1995 | Castor et al. | |
| 5,401,502 A | 3/1995 | Wunderlich et al. | |
| 5,440,055 A | 8/1995 | Castor | |
| 5,466,455 A | 11/1995 | Huffstutler, Jr. et al. | |
| 5,512,285 A | 4/1996 | Wilde | |
| 5,554,382 A | 9/1996 | Castor | |
| 5,578,307 A | 11/1996 | Wunderlich et al. | |
| 5,585,386 A | 12/1996 | Rosenbaum | |
| 5,639,441 A | 6/1997 | Sievers et al. | |
| 5,698,199 A | 12/1997 | Mori et al. | |
| 5,733,577 A | 3/1998 | Myers et al. | |
| 5,750,709 A | 5/1998 | Castor | |
| 5,770,207 A | 6/1998 | Bewicke | |
| 5,776,486 A | 7/1998 | Castor et al. | |
| 5,776,935 A | 7/1998 | Danysz et al. | |
| 5,821,450 A | 10/1998 | Fedida | |
| 5,854,064 A | 12/1998 | Castor et al. | |
| 5,877,005 A | 3/1999 | Castor et al. | |
| 5,891,465 A | 4/1999 | Keller et al. | |
| 5,906,825 A | 5/1999 | Seabrook, Jr. et al. | |
| 5,906,848 A | 5/1999 | Kreuter et al. | |
| 5,976,550 A | 11/1999 | Engel et al. | |
| 5,977,120 A | 11/1999 | Giles, Jr. | |
| 6,024,998 A | 2/2000 | Kreuter et al. | |
| 6,025,363 A | 2/2000 | Giles, Jr. | |
| 6,045,825 A | 4/2000 | Cody | |
| 6,068,846 A | 5/2000 | Cho et al. | |
| 6,080,410 A | 6/2000 | Bewicke | |
| 6,095,134 A | 8/2000 | Sievers et al. | |
| 6,117,431 A | 9/2000 | Romazanov et al. | |
| 6,140,375 A | 10/2000 | Nagahama et al. | |
| 6,143,300 A | 11/2000 | Stevenot | |
| 6,159,473 A | 12/2000 | Watkins et al. | |
| 6,174,542 B1 | 1/2001 | Hinton et al. | |
| 6,207,164 B1 | 3/2001 | Kreuter et al. | |
| 6,210,660 B1* | 4/2001 | Kripp et al. .................. 424/74 |
| 6,238,696 B1 | 5/2001 | Wang | |
| 6,238,722 B1 | 5/2001 | Meadows | |

(Continued)

FOREIGN PATENT DOCUMENTS

EP    987026    3/2000

(Continued)

OTHER PUBLICATIONS

Saldana, M.D.A. *Extraction of Methylxanthines from Guarana Seeds, Mate Leaves, and Cocoa Beans Using Supercritical Carbon Dioxide and Ethanol.* J. Argic. Food Chem. 2002, vol. 50, pp. 4820-4826.

Saldana, M.D.A. *Extraction of Purine Alkaloids from Mate (Ilex paraguariensis) Using Supercritical CO2.* J.Agric. Food Chem. 1999, vol. 47, pp. 3804-3808.

PCT International Search Report, Written Opinion of the International Searching Authority and Notification of Transmittal of same for PCT patent application No. PCT/US04/35170, filed Oct. 22, 2004.

Gosmann, G. et al., "Triterpenoid Saponins From *Ilex paraguariensis*," J. Nat Prod 58:438-441, 1995.

Filip, R. et al., "Antioxidant Activity of *Ilex paraguariensis* and Related Species," Nutr Res 20:1437-1446, 2000.

Gosmann, G. et al., "A New Saponin From Mate, *Ilex paraguariensis*," J. Nat Prod 52:1367-1370, 1989.

(Continued)

*Primary Examiner*—Susan Coe Hoffman
(74) *Attorney, Agent, or Firm*—Troutman Sanders LLP

(57) ABSTRACT

The present invention comprises methods for making compositions derived from *Ilex* species, particularly *Ilex paraguariensis*, having lowered caffeine and tannin concentrations, compositions made by such methods, oral delivery formulations, and methods of use of such compositions. In particular, the present invention comprises methods for making maté compositions that have a predetermined characteristic, such as a lowered amount of caffeine, elevated amounts of caffeoyls, and/or lowered amounts of tannin compounds compared to the native maté plant materials. Further, the invention comprises methods of additional processing steps tp produce compositions having a predetermined alkaloid ratio or profiles to meet particular considerations for final products. The compositions of the present invention may be processed for specific uses such as tablets or other oral delivery vehicles. These compositions may be used in methods for treatment of physiological and medical conditions.

24 Claims, No Drawings

U.S. PATENT DOCUMENTS

| | | |
|---|---|---|
| 6,241,988 B1 | 6/2001 | Erdelmeier et al. |
| 6,277,396 B1 | 8/2001 | Dente |
| 6,280,736 B1 | 8/2001 | Erdelmeier et al. |
| 6,288,109 B1 | 9/2001 | Chatterjee et al. |
| 6,290,985 B2 | 9/2001 | Ream et al. |
| 6,312,736 B1 | 11/2001 | Kelly et al. |
| 2002/0192241 A1 | 12/2002 | Chen et al. |
| 2003/0206974 A1 | 11/2003 | Ilic et al. |
| 2005/0118293 A1 | 6/2005 | Gow et al. |

FOREIGN PATENT DOCUMENTS

| | | |
|---|---|---|
| GB | 943121 | 11/1963 |
| WO | WO 99/61038 | 12/1999 |
| WO | WO 00/72861 | 12/2000 |

OTHER PUBLICATIONS

Saldaña, M et al., "Extraction of Purine Alkaloids from Maté (*Ilex paraguariensis*) Using Supercritical $CO_2$," J Agric Food Chem 47:3804-3808, 1999.

Goldenberg, D. et al., "The Beverage Maté: A Risk Factor For Cancer of the Head and Neck," Head & Neck 25:595-601, 2003.

Gorzalczany, S. et al., "Choleretic effect and intestinal propulsion of 'mate' (*Ilex paraguariensis*) and its substitutes or adulterants," J Ethnopharmacology 75: 291-294, 2001.

Saldaña, M et al., "Extraction of Methylxanthines from Guaraná Seeds, Maté Leaves, and Cocoa Beans Using Supercritical Carbon Dioxide and Ethanol," J Agric Food Chem 50:4820-4826.

Graham, H., "Maté," In *Caffeine* (Spiller GA, Ed.), CRC Press, Boca Raton, pp. 193-197 1998.

Filip, R et al., "Phenolic compounds in seven South American *Ilex* species," Filoterapia 72:774-778, 2001.

Carini, M. et al., "Characterization of Phenolic Antioxidants from Maté (*Ilex paraguayensis*) by Liquid Chromatography/Mass Spectrometry and Liquid Chromatography/Tandem Mass spectrometry," Rapid Comm Mass Spectrom 12:1813-1819, 1998.

Schenkel, E. et al., "Triterpene Saponins from Maté," Plenum Press, New York, 1996.

Vassallo, A. et al., "Esophageal Cancer in Uruguay: A Case-Control Study," Natl Cancer Inst 75:1005-1009, 1985.

Gugliucci A. et al., "Low Density Lipoprotein Oxication is Inhibited by Extracts of *Ilex paraguariensis*," Biochem Mol Biol Int 35:47-56, 1995.

Schinella, G. et al., "Antioxidant Effects of an Aqueous Extract of *Ilex paraguariensis*," Biochem Biophys Res Commun 269:357-360, 2000.

Baisch, A. et al., "Endothelium-dependant vasorelaxing activity of aqueous extracts of *Ilex paraguariensis* on mesenteric arterial bed of rats," J Ethnopharm 60:133-139, 1998.

De Stefani, E. et al., "*Mate* Drinking and Risk of Lung Cancer in Males: A Case-Control Study from Uruguay," Cancer Epidemiol Biomarkers Prev 5:515-519, 1996.

De Stefani, E. et al. "Black Tobacco, Maté, and Bladder Cancer, A Case-Control Study From Uruguay," Cancer 67:536-540, 1991.

Pintos, J. et al., "Maté, Coffee, and Tea Consumption and Risk of Cancers of the Upper Aerodigestive tract in Southern Brazil," Epidemiology 5:583-590,1994.

Actis-Goretta, L. et al., "Comparative Study o the Antioxidant Capacity of Wines and Other Plant-Derived Beverages," Ann N.Y. Acad Sci 957:279-283, 2002.

Cappaso, A. et al., Experimental Investigations of the Synergistic-Sedative Effect of Passiflora and Kava, Acta Therapeutica 21, 1995, pp. 127-140, vol. 21, No. 2.

Kubatova, Alena et al., Comparison of Subcritical Water and Organic Solvents for Extracting Kava Lactones from Kava Root, Journal of Chromatography, Jul. 20, 2001, pp. 187-194, vol. 923., No. 1-2, Elsevier Science Publishers B.V. Amsterdam, NL.

Rex, Andre et al., Anxiolytic-Like Effects of Kava-Kava in the Elevated Plus Maze Test—A Comparison with Diazepam, Progress in Neuro-Psychopharmacology & Biological Psychiatry, Jun. 2002, pp. 855-860, vol. 26, No. 5.

Williamson, E.M., Synergy and Other Interactions in Phytomedicines, Phytomedicine, Sep. 2001, pp. 401-409, vol. 8, No. 5.

Avila et al., Supercritical Fluid Extraction of Kava Lactones from Piper Methysticum (Kava) Herb, Journal of High Resolution Chromatography, vol. 20 (10) pp. 555-559, Oct. 1997.

Ashraf-Khorassani et al., Supercritical Fluid Extraction of Kava Lactones from Kava Root and Their Separation Via Super critical Fluid Chromatography, Chromatographia, vol. 50 (5/6) pp. 287-292, Sep. 1999.

Uy Nguyen et al., Extraction and Fractionation of Species Using Supercritical Fluid Carbon Dioxide, Presented at the 5th International Symposium on Supercritical Fluids, 1998.

* cited by examiner

METHODS AND COMPOSITIONS COMPRISING *ILEX*

RELATED PATENT APPLICATIONS

This application claims priority of U.S. Provisional Patent Application No. 60/514,187, filed Oct. 24, 2003, which is incorporated herein by reference in its entirety.

FIELD OF INVENTION

The present invention relates to methods for making compositions derived from *Ilex* species, particularly *Ilex paraguariensis*, having lowered caffeine and tannin concentrations, compositions made by such methods, oral delivery formulations, and methods of use of such compositions.

BACKGROUND OF THE INVENTION

The genus *Ilex* is member of the holly family, Aquifoliaceae, and is found worldwide in subtropical and tropical regions of both hemispheres. *I. paraguariensis* referred to as maté or yerba maté is a perennial tree indigenous to areas of southern Brazil, Argentina, Paraguay and Uruguay. It is the most commercialized plant of South America (1, 2). Aerial parts of the tree, including stems and leaves, are used to prepare a tea-like beverage known as maté or "Paraguay tea" (3). The majority of maté produced is locally consumed, with production and consumption levels highest in Argentina (4). In 1997, average annual maté consumption was 5.14 kg/person in Argentina and 6-8 kg/person in Uruguay (5). It has been estimated that 70% of adult males and 50% of adult females in South Brazil are daily maté drinkers. Approximately, 30% of the South American population consumes more than 1 liter of maté daily (2). More recently, the use of maté as a tea beverage and *Ilex* extracts as nutraceutical medicine has grown rapidly in North America and Europe.

The maté beverage is consumed primarily as an infusion, either by the addition of boiling water to the dry plant material, or by repeated additions of almost boiling water to the dry plant material. This infusion allows for extraction of water soluble plant constituents. Exposure of persons who drink maté beverage to such compounds is significant given the numbers of people and amount of maté beverage consumed. In addition to the stimulating effect of maté due to its high methylxanthine content, particularly caffeine, mate has traditionally been used as a natural medicine for arthritis, constipation, hemorrhoids, slow digestion, fatigue, hepatic disorders, headache, rheumatism, hypertension, nervous depression, improved cognition and obesity (2,6). The principal stimulant and diuretic effects of maté have been attributed to the content of caffeine (7). The estimates for caffeine intake due to maté beverage consumption far exceeds the caffeine intake known for other beverages such as coffee and tea.

One outcome of consumption of maté beverage and conventional nutraceutical *Ilex* extractions is the development of caffeine related disorders such as gastrointestinal problems, caffeine toxicity, jitteriness, generalized anxiety, and insomnia. The consumption of caffeine exaggerates stress and stress-related hormone release. Blood pressure is elevated and the risks for heart attack and stroke are increased when excessive caffeine is consumed. Because maté beverage is such a part of the social structure and cultural habits of so many people and the fact that it is being increasingly consumed as a nutraceutical medicinal agent, reducing the amount of maté consumed does not appear to be a viable method for reducing caffeine consumption.

An additional problem is that the maté that is consumed is made from raw maté plant material, which has varying amounts of caffeine when consumed drink to drink or dose to dose. This variability can cause confusing symptoms in users, hence, making the diagnosis of physiological problems difficult for clinicians. Furthermore, such variability can cause uneven results when maté is used for treatment of various physiological conditions. A issue with maté use is that clinical and epidemiological studies have found a positive association between maté consumption and cancer of the esophagus, oral cavity, pharynx, larynx, stomach, and bladder (5, 12, 17, 18, 19).

What is needed is are methods for extracting *Ilex* and *Ilex* compositions with reduced caffeine concentration having a predetermined alkaloid profile and reduced tannin constituents, and compositions that can be produced with standardized and reliable amounts of *Ilex* constituents.

SUMMARY OF INVENTION

The invention relates to methods and compositions of *Ilex* genera, particularly *I. paraguariensis*. In particular, the present invention comprises methods for making maté compositions that have a predetermined characteristic, such as a lowered amount of caffeine, elevated amounts of caffeoyls (anti-oxidants), and/or lowered amounts of the tannin compounds compared to native maté plant materials.

The compositions of the present invention comprise caffeine amounts that are lower than or equal to the amount of theobromine originally present in the native maté plant materials, and compositions comprising a predetermined amount of caffeine wherein the amount of caffeine is lower than or equal to the theobromine amount. The compositions may also comprise caffeoyl amounts greater than or equal to the amount present in the native maté plant materials and may also comprise tannin compounds in substantially reduced amounts compared to the native maté plant materials. In general, such methods comprise extraction of compounds, such as caffeine, caffeoyls, or tannin compounds from extracts of native maté plant materials or from native maté plant material using one or more extraction steps disclosed herein.

An aspect of the present invention comprises methods of selective extraction of caffeine using supercritical $CO_2$ technology different from current extraction techniques presently used on naturally derived material from *Ilex* genera.

Another aspect of the invention comprises compositions comprising extraction products that have caffeine amounts that are lower than or equal to the amount of theobromine, and compositions comprising a predetermined amount of caffeine wherein the amount of caffeine is lower than or equal to the theobromine amount. In general, such methods comprise extraction of caffeine from *Ilex* material using one or more extraction steps taught herein resulting in novel alkaloid ratios or profiles that are unlike those found in native maté plant materials or in currently known extracted compositions.

An aspect of the invention comprises methods for extracting caffeoyl compounds, and methods for extracting tannin compounds.

The invention comprises methods of additional processing steps to produce compositions having predetermined alkaloid ratio or profiles to meet particular considerations for final products.

The compositions of the present invention may comprise pastes, resins, oils, beverage, liquid infusion or decoction, powders, and dry flowable powders. Such products are processed for many different uses, including, but not limited to a fast-dissolve tablet or other oral delivery vehicles. The *Ilex* compositions taught herein can be used alone or in combination with other compounds such as other extracted botanical materials, herbal remedies, pharmaceutical agents, food, dietary supplements, or beverages. These *Ilex* compositions can be used in methods for treatment of physiological and medical conditions.

The invention comprises methods and compositions of formulations of oral delivery systems having the desired physiological and medicinal effects with reduced risks of untoward side effects. An aspect of the present invention comprises extracts of *I. paraguariensis* alone or in combination with compositions comprising maté constituents. A further aspect of the invention comprises compositions of maté extracts having a lowered caffeine concentration or an amount of caffeine that is lower in relation to the concentration or amount found in the native plant material. Another aspect of the present invention comprises compositions of extracts of *I. paraguariensis* having reduced or substantially no tannin compounds in relation to the concentration or amounts of tannin compounds found in the native maté plant material. Yet another aspect of the present invention comprises compositions of maté extracts comprising a lowered caffeine concentration and substantially no tannin compounds which also have caffeoyl concentrations that are greater or equal to the amounts of caffeoyl amounts found in the native maté plant material.

The compositions of the present invention are useful in providing the physiological effects of enhanced memory, improved cognition, reduced mental and physical fatigue, a sense of well being, appetite suppression, cardiovascular protection, providing a protective role in glycation (diabete mellitus), and beneficial effect for HIV and cancer treatment.

DESCRIPTION OF THE INVENTION

The present invention comprises methods and compositions of *Ilex* genus extracts. As used herein, *Ilex* refers to the plant or plant material derived from the plant Aquifoliaceae, *Ilex* genus, wherein the genus includes but is not limited to, *I. paraguariensis, I. theezans* C. Martis ex Reisseck, *I dumosa* Reisseck; *I dumosa* Reisseck var *dumosa; I argentina* Lillo; *I brevicuspis* Reisseck; *I microdonta* Reisseck; *I paraguariensis* St. Hil. var. *paraguaraniensis; I. paraguariensis* St. Hil. var. *vestita* (Reiss.); and *I pseudobuxus* Reisseck. The term includes all clones, cultivars, variants, and sports of *Ilex*. The term *"Ilex"* is also used interchangeably with "maté" and means these plants, clones, variants, and sports, etc. As used herein, when the tea-like beverage made from this plant genus is referred to, the beverage is designated as "maté beverage".

Purine alkaloids such as caffeine (1,3,7-trimethyl-xanthine), theobromine (3,7-dimethyl-xanthine) and theophylline (1,3-dimethyl-xanthine) are synthesized in many higher plants. It is currently believed that their synthesis pathways indicate that caffeine is primarily formed from theobromine with theophylline as an intermediate in the metabolism of caffeine.

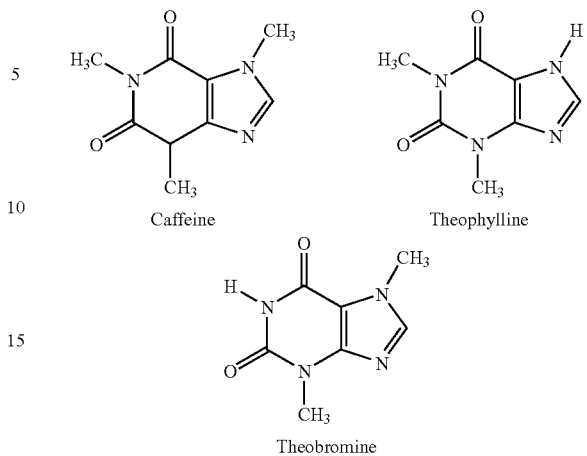

Caffeine

Theophylline

Theobromine

These three alkaloids, along with other trace methylxanthines, caffeoyl-derivatives, flavonoids, saponin glycosides, tannins, other carbohydrates and proteins, nucleic acids, lipids, vitamins, minerals, and other plant cell constituents, are found in *Ilex* plant material.

In the *Ilex* plants, the amounts of each alkaloid and the ratios of one to the others is variable and is dependent upon such factors as genetic variability, environmental conditions, harvest period, and other factors that influence the growth and chemical composition of plants. Additionally, the industrial processing methods used to make commercial products from *Ilex* plants cause further changes in the chemical constituency of the products. As used herein, the term "maté constituents" shall mean chemical compounds found in maté and shall include all such chemical compounds identified above as well as other compounds found in maté, including but not limited to caffeoyl and tannin compounds, whether derived from native *Ilex* plant materials or compounds provided by synthetic methods. The native *Ilex* plant material has variable and unknown amounts of, for instance, these alkaloid compounds, and the processing of the plant material introduces more variability in the amounts of alkaloid compounds found in the products that are consumed. This increased variability in the products consumed by the public leads to widely fluctuating physiological changes in persons ingesting such products, hinders effective treatments using *Ilex* products or prevents avoidance of unwanted physiological effects from ingestion of *Ilex* products. Native *Ilex* plant material as used herein, include plant materials that may be shredded, ground or powdered after picking and drying, but no extractions, other than incidental water or oil loss, due to the physical manipulation of the plant material, are included.

The principal bioactive chemical constituents of maté are listed in Table 1 (2, 7, 8, 9, 10, 11, 12). Beneficial effects of aqueous maté extracts include protecting low density lipoprotein (LDL) from oxidative damage as a means of inhibiting the atherosclerotic process (13). The mate effect (18.5 mM) was noted to be far greater than that measured for red wine (0.74 mM). The maté effect on inhibiting IDL oxidation has been demonstrated both in vitro and in vivo human studies (13). maté extracts have also been shown in vitro to inhibit peroxidation in a concentration dependent manner which should protect cell membrane lipids as well as having a red blood cell protectant effect against hydrogen peroxide generated free radicals (14). Based on scientific studies, the strong antioxidant effect of maté has been attributed to the caffeoyl derivatives (2). In addition to the antioxidant effects, maté has been demonstrated to play a protective role in the process of glycation (15). Glycation has been proposed as a key to diabetic complications resulting from hyperglycemia. Furthermore, the chlorogenic acids of maté have been demonstrated to be potent and selective inhibitors of HIV integrase (10) and the polyphenols have been shown to inhibit formation and growth of neoplasms (7). Finally, aqueous maté extracts were demonstrated to possess concentration-dependent vasorelaxing activity (16).

TABLE 1

Principal Bioactive Chemicals of *I. paraguariensis*

| Constituents | % Dried Weight |
|---|---|
| Methylxanthines | |
| Caffeine | 0.5-2.2 |
| Theobromine | 0.03-0.6 |
| Theophylline | 0.004-0.08 |
| Caffeoyl Derivatives | 9.0-11.0 |
| Saponin Glycosides | 5.0-10.0 |
| Tannins | 7.0-16.0 |

Theobromine is best known for its effects in chocolate products. Theobromine has been synthesized and has been used as a drug to treat different medical conditions. For example, theobromine has been used as a diuretic making it particularly useful after a person has experienced cardiac failure. Cardiac failure often results in an excess accumulation of bodily fluids. Theobromine is also known for its ability to dilate blood vessels making it a commonly prescribed treatment for people suffering from high blood pressure. In addition, theobromine is known as a weak stimulant but does not cause the jitteriness and hyper-anxiety associated with caffeine. As a stimulant, it has been noted to raise levels of serotonin making it an inexpensive anti-depressant. Theobromine is also an appetite suppressant and a useful adjunct for weight reduction. Theobromine remains in the body for a very long period of time. The half-life after ingestion is approximately 6 hours. Another rather unique property of theobromine is its ability to relax bronchi in the lungs, which also has also led to its use in the treatment of asthma and other pulmonary disorders. Theobromine has also been found to be relatively harmless in humans unless taken in excessive quantities.

Compositions of the present invention comprise extracts of maté as a paste, powder, or other forms, which allows the compounds in the extract, such as the alkaloids and caffeoyls, to be used in compositions such as dietary supplements, nutriceuticals, or pharmaceutical preparations to prevent or treat various human or animal ailments. The extracts can be processed to produce such consumable items, for example, by mixing it in a food product, in a capsule or tablet, or providing the paste itself, for use as a dietary supplement, with sweeteners or flavors added as appropriate. Accordingly, such preparations may include, but are not limited to, compositions of maté extract compositions for oral delivery in the form of tablets, capsules, lozenges, liquids, and emulsions. Other aspects of compositions of the present invention comprise maté extract compositions with or without additional theobromine in the form of a rapid-dissolve tablet.

As used herein, the term "one or more compounds" means that at least one compound, such as theobromine or chlorogenic acid or caffeic acid (caffeoyls) is intended, or that more than one compound, for example, theobromine and theophylline is intended. As known in the art, the term "compound" does not mean one molecule, but multiples or moles of molecules of one or more compounds.

The present invention comprises compositions comprising one or more compounds found in maté. The invention also comprises ingestible products that comprise the compositions comprising maté extract compositions or mate constituent compositions taught herein. For example, the present invention comprises compositions comprising a rapid dissolve tablet, comprising a maté extract composition wherein the caffeine has been reduced to amounts lower that the amounts of theobromine, and wherein the amount of tannin compounds is reduced or substantially no tannins are present. As used herein, maté extract compositions, *Ilex* extracts and maté constituent compositions can be used interchangeably unless otherwise indicated.

The present invention comprises compositions and methods for making and using such maté extract compositions and maté constituent compositions, where the compositions comprise oral delivery dosage formulations, comprising the compositions taught herein.

Steam distillation techniques that are known to those skilled in the art may be used to obtain extracts of maté from the maté plant material. The maté plant material may be the aerial portion of the plant which includes the leaves, stems, flowers, branches, twig, and trunk, or other plant parts, though leaves and stems are preferred starting material. The extract can be obtained from the maté leaves via the process of steam distillation of the leaves or by liquid extraction techniques such as, but not limited to, using ethanol, methanol, dichloromethane or petroleum ether as the extracting solvent. Alternatively, an extract of the dried leaf material can be prepared using carbon dioxide in the liquid or supercritical phase, or, a liquefied gas such as tetrafluoroethane or propane. In the case of supercritical fluid extraction (SFE) using carbon dioxide, the pressure ranges from about 1500 psi to about 10,000 psi, and in the case of liquefied gasses the pressure is an order of magnitude less ranging from about 50 psi to about 400 psi. The extract-laden liquid is then passed through a collection vessel wherein the liquefied gas can be collected as a vapor leaving behind the desirable extract that was contained in the leaf. Although the maté extract may be obtained from any species from the *Ilex* genus, the extract is preferably obtained from *I. paraguariensis*.

Alternatively, some of the chemical constituents found in maté, such as, but not limited to, caffeine, theobromine, theophylline, chlorogenic acid, caffeic acid, can be purchased individually from a chemical supply company. For example, purified theobromine that has been extracted from a natural source, such as Cacoa, may be obtained from Natra. Chemically synthesized theobromine can also be obtained from many different chemical supply companies such as Sigma Aldrich. Such individual chemical constituents found in maté may be purchased and combined with the compositions described herein. Such chemical constituents may also be mixed in the proportions that exist in maté prior to extraction or may be ratios of compounds that are not found in native maté plant material.

The present invention comprises methods for producing compositions of *Ilex* extracts that have predetermined amounts of alkaloid compounds. Embodiments comprise compositions of extracted *Ilex* having a caffeine concentration that is less than or equal to the theobromine concentration in the *Ilex* extract composition. Ranges of amounts of methylxanthines in *I. paraguariensis* from literature sources are known. For example, the amounts of methylxanthines found in the leaves of *I. paraguariensis*, on a dry weight basis range from 0.004% to 0.08% theophylline; 0.03% to 0.6% theobromine; and 0.5% to 2.2% caffeine (see Table 1), wherein the amount of caffeine is always greater than the amount of theobromine in the native plant. Compositions of the present invention comprise extracted *Ilex* compositions that have predetermined caffeine concentrations equal to or approximately less than 0.6%; approximately less than 0.55%; approximately less than 0.5%; approximately less than 0.45%; approximately less than 0.4%; approximately less than 0.35%; approximately less than 0.3%; approximately less than 0.25%; approximately less than 0.2%; approximately less than 0.15%; approximately less than 0.1%; and included ranges from 0% to less than or equal to the concentration of theobromine in the *Ilex* extract composition.

Methods for producing such compositions comprise extraction of *Ilex* plant material to alter the amount of one or more compounds from an amount or amounts found in the original plant material, such compounds may comprise alkaloid compounds, or may comprise caffeine, caffeoyls, and tannins. In regard to caffeine and tannins, *Ilex* extraction compositions may comprise significant reductions in the concentrations of these compounds when compared to the concentrations found in the native *Ilex* plant material or current extraction products of the *Ilex* genus.

The following methods as taught may be used individually or in combination with the disclosed methods or methods known to those skilled in the art. The starting material for extraction is plant material from one or more *Ilex* genera, though *I. paraguariensis* is a preferred starting material. The material may be the aerial portion of the plant, which includes the leaves, stems, branches, twigs, and trunk or other plant parts, though leaves and stems are the preferred starting material. The *Ilex* plant material may undergo pre-extraction steps to render the material into a form more easily extracted, though that form is not limited to any particular form, and any form that is useful for extraction is contemplated by the present invention. Such pre-extraction steps include, but are not limited to, wherein the material is chopped, minced, shredded, ground, pulverized, cut, or torn, and the starting material, prior to pre-extraction steps, is dried or fresh plant material. A preferred pre-extraction step comprises cutting the *Ilex* leaves and stems into small pieces known as tea cut. The starting material or material after the pre-extraction steps can be dried or can have moisture added to it. Once the *Ilex* plant material is in a form for extraction, methods of extraction are contemplated by the present invention.

One embodiment of the present invention comprises methods for extracting the maté plant material to remove one or more of the methylxanthines and optionally, other compounds found in maté. For example, an extracted maté composition may be decaffeinated, and comprise a methylxanthine concentration wherein the concentration of caffeine is less than or equal to the concentration of theobromine. Therefore, an aspect of the present invention comprises maté extract compositions or maté constituent compositions having a lower amount of caffeine in relation to the level found in conventional leaf extracts or the natural leaf material. Methods of decaffeination have been described for coffee, and are contemplated by the present invention for *Ilex* decaffeination. Descriptions of such methods are found in Katz S N. Decaffeination of Coffee. Coffee: Technology, Eds. Clark R J and Macrae R, New York, Elsevier Applied Science, 1987; and Pintauro N D. Coffee Solubilization: Commercial Process and Techniques. Park Ridge, Noyes Data Corporation, 1975; the teachings of which are incorporated herein by reference as if entirely set forth. As with coffee, the process of decaffeination of maté plant material can be accomplished in a similar fashion.

The compositions taught herein comprise maté extract compositions, compositions that result from the extraction methods taught herein. In the extraction process, there are at least two types resulting compositions, the components extracted and the material from which the components were extracted. The present invention contemplates the making and using of which may comprise maté constituent compositions and also extracted maté plant material compositions.

Other compositions of the present invention comprise extracted maté plant materials, comprising the maté plant material that undergone at least one extraction step taught herein. Embodiments of extracted plant materials comprise maté that has undergone extraction methods described herein to remove compounds so that the remaining extracted plant material has a predetermined characteristic, such as a predetermined alkaloid profile, for example, lower amounts of caffeine than that found the native maté plant materials, in the remaining extracted plant materials. An aspect of the invention comprises extracted maté plant material compositions comprising the plant material, remaining after extraction steps have been performed, having one or more of the predetermined characteristics described herein.

Methods of extraction of the present invention comprise processes disclosed herein. In general, methods of the present invention comprise, in part, novel methods wherein maté plant material is extracted using SFE (Supercritical Fluid Extraction) $CO_2$ alone (Process 1) or SFE $CO_2$ that is followed by one or more solvent extraction steps such as, but not limited to, water or hydroalcoholic extractions (Process 2) or SFE $CO_2$ extraction that is preceded by one or more solvent extractions such as, but not limited to, water or hydroethanolic extractions (Process 3).

Additional other methods contemplated for the present invention comprise extraction of maté plant materials using refrigerant chemicals or compressible gasses such as C-1 through C-4 alkane series or other known extraction methods. For example, extraction using refrigerant chemicals is known in the art. U.S. Pat. Nos. 6,455,087 and 5,512,285 teach methods of extraction using refrigerant chemical, and each is expressly incorporated in its entirety herein. Refrigerant chemicals include, but are not limited to, hydrofluorocarbons (HFCs), hydrochlorofluorocarbons (HCFCs), and/or chlorofluorocarbons (CFCs) such as: HFC-23, HFC-32, HFC-125, HFC-134a, HFC-143a, HFC-152a, R-404a, R-407c, R-410a, HCFC-22, HCFC-123, HCFC-141b, HCFC-142b, R-502, R-11, R-12, and R-113. These refrigerants are widely available from various chemical manufacturers and suppliers. Refrigerant chemicals, such as HFCs, HCFCs, and CFCs, are used in the liquid phase to perform the extraction step. During the extraction, the refrigerant chemical(s) are maintained in the liquid state and the pressure is kept below about 1000 psi. Because of the comparatively low pressure, the extraction is varied primarily by temperature. The temperature is maintained at between about 20° C. and about 70° C. The refrigerant chemicals pass through the stainless steel extraction vessel containing the maté plant material and the extract-laden liquid is deposited into a stainless steel collection vessel. The refrigerant chemical of choice can be reclaimed via collection of the refrigerant chemical in its vapor state and subsequent pressurization into the liquid state. This is in effect, a distillation process that leaves behind the plant material while recovering the refrigerant chemical as a liquid. The refrigerant chemical can then be re-cycled through the same maté plant material to repeat the process until all extractable material is removed from the maté plant material or, leveraging changes in temperature and extraction solvent, until the extract has one or more desired characteristics. A liquid polar solvent such as ethanol or other alcohols can be added to the refrigerant thus forming an azeotrope mixture to enhance the extraction efficiencies.

Although Saldana et al (4, 7) has demonstrated that SFE $CO_2$ can decaffeinate maté in an academic laboratory, the low pressures used, the time to reach equilibrium in the static extraction (3 hours) and then the time of dynamic extraction (7 hours) and solvent to feed ratio of over 328/1 as well as the use of a methanol or ethanol modifier co-solvent makes his methodology cost prohibitive for a commercial process. Typical commercial processes in high pressure SFE plants are completed within one hour for both static and dynamic parts of the cycle, and within 3 hours for low pressure SFE extraction plants. Moreover, typical solvent to feed ratios for high pressure SFE processes are typically between 15-20/1 and low pressure SFE processes are between 25-60/1. In addition, methanol is not acceptable in the nutraceutical market, due to its potential for toxicity, with ethanol as a viable co-solvent. However, ethanol in $CO_2$ is a safety problem as SFE plants are scaled up for commercially viable processing. Most large SFE facilities have banned the use of ethanol and other potentially explosive co-solvents and generally only process with nonflammable co-solvents such as water.

Supercritical $CO_2$ Process 1

Supercritical $CO_2$ Process 1 method comprises a single extraction step for differential decaffeination of maté while simultaneously preserving the other methylxanthines, particularly theobromine, in the maté plant material. This is accomplished preferably using novel SFE $CO_2$ extraction methods. For example, in a preprocessing step, the tea cut leaf maté material is pretreated with water by soaking the plant material in water until the leaves have 5% to 40% moisture content as determined by weight differential before and after heating the test material to dryness. The extractions herein are preferably performed at pressures of at least 5,000 psi and a temperature of at least 35° C., and more preferably at a pressure of about 9,000 psi to 10,000 psi and at a temperature of about 45° C. to 90° C. The maté material may be extracted in a one step process wherein the resulting extracted maté composition is collected in a one collector vessel. Alternatively, as in a fractionation system, the extracted, for example, decaffeinated, maté may be segregated into collector vessels such that within each collector there is a differing relative percentage composition of the extracted maté. An embodiment of the method comprises extracting the water-containing plant material using SFE $CO_2$ extraction at 9,000 psi to 10,000 psi and at a temperature between 45° C. and 90° C. and collecting the extracted material in differing collector vessels at predetermined intervals. The resulting extracted maté compositions in each collector vessel can be retrieved and used independently or can be combined to form one or more extracted, for example, decaffeinated, maté compositions. An aspect of the extracted maté compositions comprises a predetermined alkaloid profile, and may comprise a predetermined alkaloid profile wherein the concentration of caffeine is less than or equal to the concentration of theobromine.

A typical experimental example of this method is as follows: twenty grams of maté feedstock were ad-mixed with 28 grams of water and placed into a 100 ml SFE vessel which was connected to a Applied Separations Supercritical Fluid Extraction Unit. After purging and leak testing, the extraction vessel was brought to a pressure of 9,000 psi and a temperature of 55° C. and extracted for 180 minutes. The total extract obtained was 0.25 gm which corresponds to a yield of 1.25%. The solvent to feed ratio for the $CO_2$ was 33.01. The yield of methylxanthines was 46.88% of the total methylxanthines in the feedstock. The yield of theobromine was only 2.71% of the total theobromine in the feedstock. The yield of theophylline was 28.13%. The yield of caffeine was 66.16% of the caffeine in the feedstock clearly demonstrating that caffeine can be selectively extracted from maté utilizing this SFE $CO_2$ method with water as co-solvent.

The above example as well as numerous other confirmatory experiments provide a commercially viable process for selectively decaffeinating maté and leaving behind the theobromine and theophylline in the decaffeinated mate extract (Table 2). In general, the method comprises ad-mixing 10% to 150% water by weight with maté leaf feedstock, preferably 15% to 100%. Extraction with supercritical $CO_2$ should be carried out between 5,075 psi to 10,150 psi and preferably between 7,250 psi and 8,700 psi. Temperature may vary between 45° C. and 100° C. but preferably between 60° C. and 85° C. To achieve a caffeine yield of greater than 60% while preserving the theobromine in the maté extract product, a solvent to feed ratio between 12 to 50 is required. Greater levels of decaffeination can be achieved at higher solvent-feed ratios.

This novel and cost-effective SFE $CO_2$ selective decaffeination process for maté produces a unique methylxanthine profile with theobromine in greater concentration than caffeine. Additional SFE $CO_2$ extraction of the first stage decaffeinated maté extraction product (extraction of an extract) using an ethanol co-solvent can selectively decaffeinate mate greater than 95% of the total caffeine in the original maté plant material (feedstock). It is currently believed that the utilization of high pressure for a decaffeination process is novel, since the literature supports decaffeination processes under 350 bar. Our findings suggest that decaffeination appears to be fairly independent of the temperature or amount of water, although levels of theobromine and theophylline extracted may be sensitive to these operating conditions.

Supercritical $CO_2$ Process 2

Another process method comprises the aforementioned novel SFE $CO_2$ maté extraction methods followed by subsequent SFE $CO_2$ using a hydroethanolic co-solvent in this second step to selectively further decaffeinate the decaffeinated mate product of Process 1 (extraction of an extract product). After SFE $CO_2$ extraction methods such as those described above in Process 1 have been performed to selectively decaffeinate the maté plant feedstock material while preserving the other methylxanthines, the decaffeinated maté plant material extraction product can then undergo further selective decaffeination by other methods if desired. One such method, but not limited to, is a second step SFE $CO_2$ selective decaffeination using an hydroethanolic co-solvent. An example of such a method for additional selective extraction of caffeine from Process 1 decaffeinated maté plant material comprises the following steps: 22 gm of Process 1 decaffeinated mate was soaked with 13.2% (60% by weight of the plant material) of distilled water for 3 hours. The soaked decaffeinated maté plant material was loaded into a 100 ml SFE extraction vessel and 22.0 gm of co-solvent is used. The co-solvent was made of 17.60 gm ethanol (80% by weight of the plant material) and 4.40 gm distilled water (20% by weight of the plant material). The SFE $CO_2$ extraction was performed at 9500 psi and 90° C. for 60 minutes at 6 liters/min. Using this process, greater than 95% of the caffeine was selectively removed from the Process 1 partially decaffeinated (60%) maté extraction material while preserving the other methylxanthines. Hence, using a Process 2 method on the Process 1 decaffeinated maté product can increase the selective decaffeination from 66% decaffeination to greater than 95% decaffeination of the maté plant material.

In general, the decaffeinated maté plant material that was extracted with either SFE $CO_2$ via Process 1 or 2 is recovered and further extracted with solvent extraction methods known to those skilled in the art such as, but not limited to, water or hydroethanolic solutions. For example, any one of, but not limited to, three methods well known to those skilled in the art are described below. An aspect of the compositions made using these methods is a composition comprising an altered alkaloid profile, and preferably an alkaloid profile wherein the amount of caffeine is less than or equal to the amount of theobromine in the composition. Further extractions methods, such as the solvent extraction methods below, retrieve and concentrate the altered alkaloid compositions and the bioactive and beneficial caffeoyl constituents while removing the toxic maté tannins from maté extraction products.

In one method, decaffeinated maté material is mixed into either a distilled water or a hydroethanolic solution, for example, 50% to 95% ethanol content in distilled water, and preferably between 65% and 85% ethanol content in a ratio of solution to decaffeinated maté material (liters:kg) ranging from 2:1 to 20:1. The mixture of decaffeinated maté material and liquid solution is heated from 20° C. to 60° C., and mixed for a period of time of between 1 hour and 12 hours. One method for mixing comprises using a kettle that is jacketed such that the temperature is controlled. The kettle is closed and the mixture is stirred slowly. After the desired time of mixing, the liquid is separated from the solid material by means known to those skilled in the art, including but not limited to, filtration or centrifugation. The remaining solid material may be further extracted one or more times by the above steps of solute extractions, heating and mixing to yield extracted maté compositions that can be used independently or can be pooled with other extracted maté compositions. Alternatively, the resulting material from the solute extractions can undergo SFE $CO_2$ extraction, refrigerant extraction, or other extractions to yield extracted maté compositions that can be used independently or pooled with other maté compositions. An aspect of the compositions made using this method is a composition comprising an altered alkaloid profile, and preferably an alkaloid profile wherein the amount of caffeine is less than or equal to the amount of theobromine in the composition. A further embodiment of the composition is a caffeoyl concentration of the dried extract that is by mass weight equal to or greater than the caffeoyl concentration in the maté natural leaves or feedstock.

A further embodiment of a solute extraction method of the present invention comprises using solutions such as, but not limited, water or alcohol or hydroalcoholic solutions in a Soxhlet or pseudo-Soxhlet extraction process. The Soxhlet extraction process is a well known method for extracting materials. The Soxhlet extraction process or pseudo-Soxhlet extraction process can occur under normal atmospheric or reduced atmospheric pressure. In the Soxhlet extraction, the decaffeinated leaf material is held apart from the reservoir of the solvent and a condenser element is above the leaf material onto which the solvent condenses and drips onto, into, and through the leaf material making the extract that condenses in the reservoir below. This extraction process can be performed with water or alcohol (or other solvent) alone, sequentially with water first and alcohol thereafter or visa versa with subsequent pooling of the extracts, or a hydroalcoholic solution, which is 50% to 90% ethanol content in water, and preferably between 60% and 80% ethanol content. The resulting extracted maté composition from the Soxhlet extraction methods can undergo further extractions, including but not limited to, SFE $CO_2$, refrigerant extraction or other extractions such as detannization (see below), to yield extracted maté compositions. The remaining solid decaffeinated maté material may also be further extracted one or more times by the Soxhlet extraction methods, or other extraction methods, to yield extracted maté compositions that can be used independently or pooled with other extracted maté compositions. An aspect of the compositions made using this method is a composition comprising an altered alkaloid profile, and preferably an alkaloid profile wherein the amount of caffeine is less than or equal to the amount of theobromine in the composition. Another aspect of present invention's composition is a caffeoyl concentration of the dried composition extract that is by mass weight greater than the caffeoyl concentration in the maté natural leaf material (see Table 2).

Another embodiment of the solvent extraction methods using, but not limited to water or hydroalcoholic solutions comprises extraction under pressure from 50 to 2,500 pounds per square inch (psi). For example, the decaffeinated maté plant material is contained within a vessel that can be pressurized. The vessel is first evacuated so that the heated water or hydroalcoholic solution can be drawn into the vessel and then an appropriate pump brings the solution up to the desired pressure. The mixture is brought to the desired temperature, preferably between 20 degree C. and 90 degree C., and to the desired pressure, preferably between 50 psi and 1,500 psi. The mixture remains at that pressure and temperature for a desired amount of time, preferably 0.5 hours to 4 hours. There can be some slight fluctuation in the temperature and pressure, in a range of about 10%, but preferably the mixture stays at a steady state. After the material is extracted, the liquid is removed and collected. The plant material may be extracted one or more times using this method. The resulting extracted maté compositions can be pooled or used independently. The resulting extracted maté composition from this extraction method can undergo further extractions, including but not limited to, SFE $CO_2$, refrigerant extraction, or other extractions such as detannization, to yield extracted maté compositions that can be used independently or pooled with other extracted maté compositions. An aspect of the compositions made using this method is a composition comprising an altered alkaloid profile, and preferably an alkaloid profile wherein the amount of caffeine is less than or equal to the amount of theobromine in the composition. Another aspect of the composition is a caffeoyl concentration of the dried mate extract composition that is by mass weight equal to or greater than the caffeoyl concentration in the native maté plant material.

Following the selective decaffeination of native maté plant material and solvent extraction of the decaffeinated maté extract material, the maté composition in solution can undergo detanninization in order to substantially reduce the concentration of potentially harmful maté tannin compounds in relation to the level found in the native plant material or in conventional maté extracts and beverages. To remove the tannins or tannin compounds from the decaffeinated maté extract, absorbents such as, but not limited to, proteins (e.g., egg albumen, casein, gelatin), activated carbons or charcoal, absorbent exchange resins absorbent (amberlite XAD 1180 resin, polyvinyl polypyrrolidone-PVPP, polyethylene glycol-PEG, Sephadex LH20), bentonite, silicon dioxide (isinglass), alginic acid and molecular imprinted polymers. For those skilled in the art, the removal of tannins and other large molecular weight compounds through the addition of such absorbents is accomplished in a straight forward manner and is well documented in industry, particularly the wine industry. The use of proteins for removal of the tannins has great advantage due to their high specificity for binding tannins without removal of the smaller polyphenolic compounds such as the important caffeoyls in maté. Protein characteristics that favor strong bonding with tannins include large molecular size, open and flexible structures, richness in proline, and a positive charge at neutral or low pH. Tannin characteristics that favor strong bonding with protein include high molecular weight, high conformational mobility, and excellent hydrogen bonds that form strong hydrogen bonds with the protein's carboxyl group. Hydrophobic bonds are stronger at higher ionic strength (higher tannin/protein ratios) and higher temperatures leading to precipitation of the tannin compounds. Although proteins have an affinity for polyphenols reacting by forming hydrogen bonds between the phenolic hydroxyl and the peptide bonds of the protein component, the large polyphenols such as the tannins and polymerized anthocyanins are preferentially removed. An example of removal of the tannins from the maté composition extract is as follows: In step 1, the SFE $CO_2$ decaffeinated mate extract material (see Table 2) underwent a 60 weight % ethanol/water Soxhlet extraction for 18 hours with a yield of 39% by mass weight of the extraction composition. In step 2. albumen protein (4 mg albumen/1 gm extract composition) was incrementally added to the solution of decaffeinated extraction composition and allowed to sit for 12 hours. The precipitated protein-tannin complexes were then filtered out leaving the detanninzed, decaffeinated maté extraction composition with an enhanced concentration of caffeoyls as measured by the chlorogenic acid concentration (Table 2). The final maté composition product is obtained by drying using any of a variety of methods to be discussed.

TABLE 2

Exemplary Example of Extraction Steps of *I. paraguariensis*

| | *I. paraguariensis* constituent by % dry weight | | | | |
|---|---|---|---|---|---|
| | Caffeine | Theo-bromine | Theo-phylline | Chlorogenic Acid | Tannins |
| Feedstock | 2.0 | 0.5 | 0.1 | 2.8 | 14.9 |
| SFE CO2 Extract | 0.8 | 1.1 | 0.2 | 2.8 | 13.7 |
| Hydroethanolic Extract | 2.1 | 2.8 | 0.5 | 8.6 | 7.9 |
| Detannization Extract | 2.0 | 2.6 | 0.5 | 8.4 | 3.4 |

Supercritical $CO_2$ Process 3

A further method for making maté extract compositions comprises solute extraction of the maté feedstock (dried maté native plant material) including the detannization of the maté extraction product while the maté composition is in solution as described in the preceding sections of this manuscript. In this method, any one of the above solute extraction methods can be used followed by one of the above detannization methods to produce a detannized maté composition that preserves or increases the concentration of the maté caffeoyls. This extracted maté composition is then dried by methods known to those skilled in the art such as, but not limited to, freeze drying or spray drying. The dried detanninized mate extract composition is then further processed with SFE $CO_2$ as described in Process 1, or by utilizing a process that involves the use of SFE $CO_2$ in a counter-current fashion wherein the SFE $CO_2$ is contained within polypropylene tubes that are immersed within the hydroalcoholic extract solution of the maté. For example, the SFE $CO_2$ extraction methods are used to selectively decaffeinate the detannized maté extract material to a prescribed level and can also remove the alcohol. Thereafter, the liquid containing the final maté extraction composition can be taken to dryness by suitable means.

Many methods are known in the art for removal of alcohol from solution. If it is desired to keep the alcohol, the alcohol can be removed from the solutions, after extraction, by distillation under normal or reduced atmospheric pressures. The alcohol can then be reused.

There are also many methods known in the art for removal of water from solutions, either aqueous solutions or solutions from which the alcohol was removed. Such methods include, but not limited to, by spay drying the aqueous solutions onto a suitable carrier such as, but not limited to, magnesium carbonate or maltodextrin, or alternatively, the liquid can be taken to dryness by freeze drying or refractive window drying. If the water is not removed by drying, where the extract is kept in solution and not dried, methods such as those taught in U.S. Pat. No. 5,490,884 is used to remove the caffeine in a continuous flow counter-current fashion.

In performing the previously described extraction methods, it was found that the dried bulk extract of the leaves of *I. paraguariensis* amounts to between 10% and 30% by weight of the original dried *I. paraguariensis* leaves used. Using extraction methods such as those described above, the desired alkaloid profiles are created in the extracted maté compositions or in the extracted plant material compositions. Alternatively, the maté plant material could be extracted to remove one, two, or all or almost all of at least three methylxanthines (caffeine, theobromine, and theophylline) to produce either an extracted maté composition substantially free of one or more of these compounds, or to produce a composition comprised of at least one, two, or three methylxanthines. The specific extraction environments, rates of extraction, and solvents used depend on the starting profile of the source material and the degree of profile change desired. Specific solvent and environmental attributes can be determined by those of ordinary skill in the art using no more than routine experimentation typical for adjusting a process to account for sample variations in the attributes of starting materials that is to be processed to produce an output material that has specified attributes. For example, in a particular lot of maté plant material, the initial concentrations of caffeine, theobromine and theophylline are determined using methods known to those skilled in the art, such as extraction and measurement of each using, but not limited to, high performance liquid chromatography (HPLC). One skilled in the art can determine the amount of change from the initial concentrations of the methylxanthines to the predetermined amounts of methylxanthines for the final extraction product using the extraction methods, as disclosed herein, to reach the desired profile of the final maté composition.

Similarly, HPLC is used to determine the concentration of the maté caffeoyls in the mate feedstock and during the extraction processes by measuring caffeoyl component compounds such as chlorogenic acid and/or caffeic acid in order to verify the caffeoyl concentration desired in the final maté product. Finally, the tannin concentration in the feedstock and the various extraction products can be measured using a variety of assays know to those skilled in the art such as, but not limited to, colorimetric assays (Folin-Dennis method, Folin-Ciocalteau method, vanilla-HCl assay, butanol-HCl assay, rhodanine assay, Wilson & Hagerman assay), gravimetric assays (ytterbium methods, PVP method, detergent system method), protein precipitation assay (radial diffusion assay), and mixed assay (Giner-Chavez method). The tannin data herein was derived from the Folin-Ciocalteau method which is capable of measuring the total free phenolic groups, particularly the total soluble phenolics.

In general, the methods and compositions of the present invention comprise methods for making an extracted maté composition having predetermined characteristics. SFE $CO_2$ methods and conditions are used until a composition comprising a predetermined alkaloid composition is obtained. Embodiments comprise methods wherein the predetermined characteristic comprises a predetermined selectively reduced (decaffeinated) caffeine concentration, and preferably wherein the predetermined caffeine concentration is a concentration that is less than or equal to the theobromine concentration. Methods further comprise performing a solute extraction including detannization before or after the SFE $CO_2$ extractions. Compositions resulting from such methods comprise extracted maté plant material or an extracted maté composition, or combination or mixtures of both. Compositions comprise extracted maté plant material having a predetermined characteristic or an extracted maté composition having a predetermined characteristic. An embodiment of such compositions comprise a predetermined caffeine concentration wherein the predetermined caffeine concentration is a concentration of caffeine that is less than or equal to the theobromine concentration which can result from the extraction techniques taught herein. A second embodiment of such compositions comprises a caffeoyl concentration in the extracted maté composition that is equal to or greater than the concentration found in the natural dried maté plant material or conventional maté extracts or maté beverages. A third embodiment of such compositions comprises a tannin concentration substantially reduced in the extracted maté composition compared to the natural dried maté plant material or conventional maté extracts or maté beverages.

In the present invention, methods and compositions are contemplated for making maté compositions having at least one predetermined characteristic, comprising, extracting native maté plant material using supercritical $CO_2$ conditions to obtain maté compositions comprising at least one predetermined characteristic. It is further contemplated that at least one predetermined characteristic comprises, though is not limited to, a reduction in the caffeine concentration, wherein the caffeine concentration is less than or equal to the theobromine concentration; caffeoyl derivative concentrations, wherein the caffeoyl derivative concentration, by per cent mass weight, is greater than the native mate plant material caffeoyl derivative concentration; or tannin concentrations, wherein the tannin concentration is less than 50% by mass weight than the native maté material. Methods further comprise that the supercritical $CO_2$ conditions selectively decaffeinate maté leaves or maté extraction compositions so that the amounts of theobromine and theophylline are not substantially changed, and comprise conditions wherein the supercritical fluid $CO_2$ conditions comprise a pressure of between about 5,000 psi to about 10,00 psi and an operating temperature between 45° C. and 100° C. or that water is used as a cosolvent at 10% to 150% water by weight with maté leaf feedstock, preferably 15% to 100%, or alternatively that the supercritical fluid $CO_2$ is at a pressure of between 5,075 psi to 10,150 psi and an operating temperature between 45° C. and 100° C., water is used as a cosolvent at 10% to 150% water by weight with maté leaf feedstock, preferably 15% to 100%, so that caffeine is selectively extracted while other methylxanthines are minimally extracted. Methods further comprise water or hydroalcoholic extraction of native maté plant material before or after the supercritical $CO_2$ conditions.

In the present invention, maté compositions are contemplated, comprising, extracted mate plant material having at least one predetermined characteristic. It is further contemplated that at least one predetermined characteristic may comprise, though not be limited to only these listed herein, a predetermined caffeine concentration, wherein the predetermined caffeine concentration is a caffeine concentration that is less than or equal to the theobromine concentration; a caffeoyl derivative concentration, wherein the caffeoyl derivative concentration, by per cent mass weight, is greater than the native mate plant material caffeoyl derivative concentration; or a tannin concentration, wherein the tannin concentration is less than 50% by mass weight than the native mate material. It is further contemplated that at least one predetermined characteristic comprises a caffeine concentration that is less than or equal to the theobromine concentration; a caffeoyl derivative concentration that is greater, by per cent mass weight, than native mate plant material; and a tannin concentration of less than 50% by mass weight compared to the native mate plant material.

According to a further aspect of the invention, the extracted maté plant material or an extracted maté composition can be further processed to dry, flowable powder. The powder can be used as a dietary supplement that can be added to various edible products. The powder or the final predetermined unique extract of maté is also suitable for use in a rapid dissolve tablet.

According to a particular aspect of the present invention, the extracted maté compositions are produced to have a predetermined alkaloid profile (preferably having a caffeine concentration less than or equal to the concentration of theobromine), caffeoyl concentration (preferably greater concentration than that found in the natural plant material or conventional maté extracts), and reduced tannin concentration (preferably substantially lower than the concentration found in the natural plant material or conventional maté extracts), that is, particularly well suited for delivery in the oral cavity of human subjects, e.g., via a rapid dissolve tablet.

In one embodiment of a method for producing a maté extraction powder, a dry extracted maté composition is mixed with a suitable solvent, such as but not limited to water or ethyl alcohol, along with a suitable food-grade material using a high shear mixer and then spray air-dried using conventional techniques to produce a powder having grains of very small maté extract particles combined with a food-grade carrier.

In a particular example, an extracted maté composition is mixed with about twice its weight of a food-grade carrier such as maltodextrin having a particle size of between 100 to about 150 micrometers and an ethyl alcohol solvent using a high shear mixer. Inert carriers, such as silica, preferably having an average particle size on the order of about 1 to about 50 micrometers, can be added to improve the flow of the final powder that is formed. Preferably, such additions are up to 2% by weight of the mixture. The amount of ethyl alcohol used is preferably the minimum needed to form a solution with a viscosity appropriate for spray air-drying. Typical amounts are in the range of between about 5 to about 10 liters per kilogram of extracted maté material. The solution of extracted maté composition, maltodextrin and ethyl alcohol is spray air-dried to generate a powder with an average particle size comparable to that of the starting carrier material.

In a second embodiment, an extracted maté composition and food-grade carrier, such as magnesium carbonate, a whey protein, or maltodextrin are dry mixed, followed by mixing in a high shear mixer containing a suitable solvent, such as water or ethyl alcohol. The mixture is then dried via freeze drying or refractive window drying. In a particular example, an extracted maté composition is combined with food grade material about one and one-half times by weight of the extracted maté composition, such as magnesium carbonate having an average particle size of about 20 to 200 micrometers. Inert carriers such as silica having a particle size of about 1 to about 50 micrometers can be added, preferably in an amount up to 2% by weight of the mixture, to improve the flow of the mixture. The magnesium carbonate and silica are then dry mixed in a high speed mixer, similar to a food processor-type of mixer, operating at 100 s of rpm. The extracted maté composition is then heated until it flows like a heavy oil. Preferably, it is heated to about 50° C. The heated extracted maté composition is then added to the magnesium carbonate and silica powder mixture that is being mixed in the high shear mixer. The mixing is continued preferably until the particle sizes are in the range of between about 250 micrometers to about 1 millimeter. Between about 2 to about 10 liters of cold water (preferably at about 4 degree C.) per kilogram of extracted maté composition is introduced into a high shear mixer. The mixture of extracted mate composition, magnesium carbonate, and silica is introduced slowly or incrementally into the high shear mixer while mixing. An emulsifying agent such as carboxymethylcellulose or lethicin can also be added to the mixture if needed. Sweetening agents such as sucralose or acesulfame K up to about 5% by weight can also be added at this stage if desired, Alternatively, extract of *Stevia rebaudiana*, a very sweet-tasting dietary supplement, can be added instead of or in conjunction with a specific sweetening agent (for simplicity, Stevia will be referred to herein as a sweetening agent). After mixing is completed, the mixture is dried using freeze-drying or refractive window drying. The resulting dry flowable powder of extracted maté composition, magnesium carbonate, silica and optional emulsifying agent and optional sweetener has an average particle size comparable to that of the starting carrier with the predetermined characteristic(s) of the extracted maté composition.

According to another embodiment, an extracted maté composition is combined with approximately an equal weight of food-grade carrier such as whey protein, preferably having a particle size of between about 200 to about 1000 micrometers. Inert carriers such as silica having a particle size of between about 1 to about 50 micrometers, or carboxymethylcellulose having a particle size of between about 10 to about 100 micrometers can be added to improve the flow of the mixture. Preferably, an inert carrier addition is no more than about 2% by weight of the mixture. The whey protein and inert ingredient are then dry mixed in a food processor-type of mixer that operates over 100 rpm. The maté extraction composition is heated until it flows like a heavy oil (preferably heated to 50 degree C.). The heated maté extraction composition is then added incrementally to the whey protein and inert carrier that is being mixed in the food processor-type mixer. The mixing of the maté extraction composition and the whey protein and inert carrier is continued until the particle sizes are in the range of about 250 micrometers to about 1 millimeter. Next, 2 to 10 liters of cold water (preferably at about 4 degree C.) per kilogram of the paste mixture is introduced in a high shear mixer. The mixture of maté extraction composition, whey protein, and inert carrier is introduced incrementally into the cold water containing high shear mixer while mixing. Sweetening agents or other taste additives of up to 5% by weight can be added at this stage if desired. After mixing is completed, the mixture is dried using freeze drying or refractive window drying. The resulting dry flowable powder of maté extraction composition, whey protein, inert carrier and optional sweetener has a particle size of about 150 to about 700 micrometers and an unique predetermined mate extraction composition.

In a further embodiment, a predetermined maté extraction composition is dissolved in a SFE $CO_2$ fluid which is then absorbed onto a suitable food-grade carrier such as maltodextrin, dextrose, or starch. Preferably, the SFE $CO_2$ is used as the solvent. Specific examples include starting with an extracted maté composition and adding from 1 to 1.5 times the extracted maté material by weight of the food-grade carrier having a particle size of between about 100 to about 150 micrometers. This mixture is placed into a chamber containing mixing paddles and which can be pressurized and heated. The chamber is pressurized with $CO_2$ to a pressure in the range between 1100 psi to about 8000 psi and set at a temperature in the range of between about 20° C. to about 100° C. The exact pressure and temperature are selected to place the $CO_2$ in a supercritical fluid state. Once the $CO_2$ in the chamber is in the supercritical state, the maté extraction composition is dissolved. The mixing paddles agitate the carrier powder so that it has intimate contact with the supercritical $CO_2$ that contains the dissolved maté material. The mixture of supercritical $CO_2$, dissolved maté extraction material, and the carrier powder is then vented through an orifice in the chamber which is at a pressure and temperature that does not support the supercritical state for the $CO_2$. The $CO_2$ is thus dissipated as a gas. The resulting powder in the collection vessel is the carrier powder impregnated with the predetermined maté extraction composition. The powder has an average particle size comparable to that of the starting carrier material. The resulting powder is dry and flowable. If needed, the flow characteristics can be improved by adding inert ingredients to the starting carrier powder such as silica up to about 2% by weight as previously discussed.

In the embodiments where the extract of maté with a predetermined composition or profile is to be included into a oral fast dissolve tablet as described in U.S. Pat. No. 5,298,261, the unique extract can be used "neat", that is, without any additional components which are added later in the tablet forming process as described in the patent cited. This method, then obviates the necessity to take the unique maté extract to a dry flowable powder that is then used to make the tablet.

Once a dry maté extraction powder is obtained, such as by the methods discussed herein, it can be distributed for use, e.g., as a dietary supplement or for other uses. In a particular embodiment, the maté extraction composition powder is mixed with other ingredients to form a tableting composition of powder which can be formed into tablets. The tableting powder is first wet with a solvent comprising alcohol, alcohol and water, or other suitable solvents in an amount sufficient to form a thick doughy consistency. Suitable alcohols include, but not limited to, ethyl alcohol, isopropyl alcohol, denatured ethyl alcohol containing isopropyl alcohol, acetone, and denatured ethyl alcohol containing acetone. The resulting paste is then pressed into a tablet mold. An automated tablet molding system, such as described in U.S. Pat. No. 5,407,339, can be used. The tablets can then be removed from the mold and dried, preferably by air-drying for at least several hours at a temperature high enough to drive off the solvent used to wet the tableting powder mixture, typically between about 70° C. to about 85° C. The dried tablet can then be packaged for distribution.

Methods and compositions of the present invention comprise compositions comprising unique maté extract compositions in the form of a paste, resin, oil, or powder. An aspect of the present invention comprises compositions of liquid preparations of unique maté extract compositions. Liquid preparations for oral administration may take the form of, for example, solutions, syrups or suspensions, or they may be presented as a dry product for reconstitution with water or other suitable vehicle prior to administration. Such liquid preparations may be prepared by conventional means with pharmaceutically acceptable additives such as suspending agents (e.g., sorbitol syrup, methyl cellulose, or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners. Compositions of the liquid preparations can be administered to humans or animals in pharmaceutical carriers known to those skilled in the art. Such pharmaceutical carriers include, but are not limited to, capsules, lozenges, syrups, sprays, rinses, and mouthwash.

An aspect of the present invention comprises compositions of a dry powder mate extraction composition. Such dry powder compositions may be prepared according to methods disclosed herein and by other methods known to those skilled in the art suchas, but not limited to, spray air drying, freeze drying, vacuum drying, and refractive window drying. The combined dry powder compositions can be incorporated into a pharmaceutical carrier such, but not limited to, tablets or capsules, or reconstituted in a beverage such as a tea.

Although the extraction techniques described herein are discussed in terms of maté, it should be recognized that compositions of the present invention can also comprise, in the form of a dry flowable powder or other forms, extracts from other plants such as, but not limited to, varieties of ginseng, cherry, lettuce, Echinacia, piper betel leaf, Areca catechu, muira puama, ginger, willow, suma, kava, horny goat weed, ginko bilboa, turmeric, garlic, puncture vine, arctic root astragalus, eucommia, gastropodia, and uncaria, or pharmaceutical or nutriceutical agents.

The present invention comprises compositions comprising unique maté extract compositions in tablet formulations and methods for making such tablets. A tableting powder can be formed by adding about 1% to 40% by weight of the powdered maté extract composition, with between 30% to about 80% by weight of a dry water-dispersible absorbant such as, but not limited to, lactose. Other dry additives such as, but not limited to, one or more sweetener, flavoring and/or coloring agents, a binder such as acacia or gum arabic, a lubricant, a disintegrant, and a buffer can also be added to the tableting powder. The dry ingredients are screened to a particle size of between about 50 to about 150 mesh. Preferably, the dry ingredients are screened to a particle size of between about 80 to 100 mesh.

The present invention comprises compositions comprising tablet formulations and methods for making such tablets. Preferably, the tablet has a formulation that results in a rapid dissolution or disintegration in the oral cavity. The tablet is preferably a homogeneous composition that dissolves or disintegrates rapidly in the oral cavity to release the extract content over a period of about 2 seconds or less than 60 seconds or more, preferably about 3 to about 45 seconds, and most preferably between about 5 to about 15 seconds.

Various rapid-dissolve tablet formulations known in the art can be used. Representative formulations are disclosed in U.S. Pat. Nos. 5,464,632; 6,106,861; 6,221,392; 5,298,261; 6,221,392; and 6,200,604; the entire contents of each are expressly incorporated by reference herein. For example, U.S. Pat. No. 5,298,261 teaches a freeze-drying process. This process involves the use of freezing and then drying under a vacuum to remove water by sublimation. Preferred ingredients include hydroxyethylcellulose, such as Natrosol from Hercules Chemical Company, added to between 0.1% and 1.5%. Additional components include maltodextrin (Maltrin, M-500) at between 1% and 5%. These amounts are solubilized in water and used as a starting mixture to which is added the maté extraction composition, along with flavors, sweeteners such as Sucralose or Acesulfame K, and emulsifiers such as BeFlora and BeFloraPlus which are extracts of mung bean.

A particularly preferred tableting composition or powder contains about 10% to 60% by of the maté extract composition powder and about 30% to about 60% of a water-soluble diluent. Suitable diluents include lactose, dextrose, sucrose, mannitol, and other similar compositions. Lactose is a preferred diluent but mannitol adds a pleasant, cooling sensation and additional sweetness in the mouth. More than one diluent can be used. A sweetener can also be included, preferably in an amount between 3% to about 40% by weight depending on the desired sweetness. Preferred sweetening substances include sugar, saccharin, sodium cyclamate, aspartame, and Stevia extract used singly or in combination, although other sweeteners could alternatively be used. Flavoring such as mint, cinnamon, citrus (e.g., lemon or orange), mocha, and others can be also included, preferably in an amount between about 0.001% to about 1% by weight. If a coloring is desired, natural and/or synthetic colors can be added, preferably in an amount of between about 0.5% to about 2% by weight.

Typically, this tableting composition will maintain its form without the use of a binder. However, if needed, various binders are suitable and can be added in an amount of between about 5% to about 15% or as necessary. Preferred binders are acacia or gum arabic. Alternative binders include sodium alginate, extract of Irish moss, panwar gum, ghatti gum, mucilage of isapol husks, carboxymethylcellulose, hydroxyethylcellulose, methylcellulose, polyvinylpyrrolidone, VEEGUM.®™ (available from R. T. Vanderbilt Co., Inc. of Norwalk, Conn.), larch arabogalactan, gelatin, Kappa carrageenan, copolymers of maleic anhydride with ethylene or methyl ether.

A tablet according to this aspect of this invention typically does not require a lubricant to improve the flow of the powder for tablet manufacturing. However, if it is so desired, preferred lubricants include talc, magnesium stearate, calcium stearate, stearic acid, hydrogenated vegetable oils, and carbowax in amount of between about 2% to about 10% by weight.

Similarly, a disintegrant does not appear necessary to produce rapid dissolve tablets using the present tablet composition. However, a disintegrant can be included to increase the speed with which a resulting tablet dissolves in the mouth. If desired, between about 0.5% to about 1% by weight of a disintegrant can be added. Preferred disintegrants include starches, clays, cellulose, algins, gums, crosslinked polymers (including croscarmelose, crospovidone, and sodium starch glycolate), VEEGUM.RTM. HV, agar, bentonite, natural sponge, cation exchange resins, aliginic acid, guar gum, citrus pulp, sodium lauryl sulphate in an amount of about 0.5% to about 1% of the total mass of the tablet.

It is also generally unnecessary to buffer the tablet composition. However, a buffer may be beneficial in specific formulations. Preferred buffering agents include mono- and di-sodium phosphates and borates, basic magnesium carbonate and combinations of magnesium and aluminum hydroxide.

In a preferred implementation, the tableting powder is made by mixing in a dry powdered form the various components as described above, e.g., active ingredient (maté extract), diluent, sweetening additive, and flavoring, etc. An overage in the range of about 10% to about 15% of the active extract of the active ingredient can be added to compensate for losses during subsequent tablet processing. The mixture is then sifted through a sieve with a mesh size preferably in the range of about 80 mesh to about 100 mesh to ensure a generally uniform composition of particles.

The tablet can be of any desired size, shape, weight, or consistency. The total weight of the maté extract composition in the form of a dry flowable powder in a single oral dosage is typically in the range of about 80 mg to about 600 mg. An important consideration is that the tablet is intended to dissolve in the mouth and should therefore not be of a shape that encourages the tablet to be swallowed. The larger the tablet, the less it is likely to be accidentally swallowed, but the longer it will take to dissolve or disintegrate. In a preferred form, the tablet is a disk or wafer of about 0.15 inch to about 0.5 inch in diameter and about 0.08 inch to about 0.2 inch in thickness, and has a weight of between about 160 mg to about 1,200 mg. In addition to disk, wafer or coin shapes, the tablet can be in the form of a cylinder, sphere, cube, or other shapes. For example, the tablet can be formed into the general shape of a maté plant leaf. Although the tablet is preferably homogeneous, the tablet may alternatively be comprised of regions of powdered maté extract composition separated by non-maté extract regions in periodic or non-periodic sequences, which can give the tablet a speckled appearance with different colors or shades of colors associated with the maté extract regions and the non-maté extract regions.

Compositions of maté extract compositions may also comprise maté compositions in an amount between about 10 mg and about 750 mg per dose. The maté alkaloid composition of the maté extract composition can vary wherein caffeine is in an amount between about 0.1 mg and about 5.0 mg, theobromine is in an amount between about 0.2 mg and about 8.0 mg, and theophylline is in an amount between about 0.01 mg and about 3.0 mg. The maté caffeoyl composition of the maté extract compositions can vary between about 1.0 mg and about 150 mg per dose wherein the % mass weight of the caffeoyl constituents in the unique maté extraction composition are greater than that found in the natural maté leaf material or conventional mate extracts and beverages. The maté tannin composition of the maté extract composition can vary between about 1.0 mg and about 75 mg wherein the % mass weight of the tannin constituents are less than 80% (preferably less than 20%) of the maté tannin concentration found in the native maté plant material or conventional maté extracts or beverages. Finally, naturally derived or synthesized theobromine may be used to supplement the theobromine content of the maté extraction compositions in an amount between about 0.1 mg and 500 mg.

An exemplary 275 mg tablet contains about 150.0 mg powdered maté extract composition, about 12.5 mg extract of Stevia, about 35.5 mg carboxymethylcellulose, and about 77.0 mg of lactose (see Example 1). Additional exemplary formations for 240 mg and 350 mg maté extraction composition tablets can be found in Examples 2 and 3.

The present invention comprises methods of using compositions comprising unique maté extraction compositions disclosed herein. Methods of providing dietary supplementation are contemplated. Such compositions may further comprise vitamins, minerals and antioxidants. Compositions taught herein can also be used in the methods of treatment of conditions wherein a diuretic, relaxant or vasodilator, or bronchial dilator would be effective. For example the present invention comprises methods for the treatment of asthma or obstructive pulmonary disease (COPD), comprising administrating an effective amount of a combination composition taught herein. Methods of treatment of conditions in which a stimulant to the central nervous system would be effective or treatment of rheumatic conditions are also contemplated by the present invention.

The maté extraction compositions of the present invention are used to prevent and treat cardiovascular and cerebrovascular disease. The maté extraction compositions are used to provide antioxidant activity to human and animals, cells and cell membranes and protect low density lipoprotein from oxidative damage. Pathologies that are related to oxygen radical damage include, but not limited to, cardiovascular disease, cerebrovascular disease (stroke), arthritis, inflammation, hepatic disorders, HIV, and cancer. Moreover, the maté extraction compositions of the present invention are used to play a protective role in the process of glycation which is key to the prevention of complications resulting from hyperglycemia. These and other related pathologies are prevented or treated by administering an effective amount of the maté extraction composition of the present invention.

The maté compositions of the present invention are also useful for the treatments of obesity and as an aid to weight loss. Methods of the present invention comprise treatments for obesity and methods for enhancing weight loss comprising administration of an effective amount of a maté extraction composition, such an amount being effective in reduction of weight of a human or animal.

The maté extraction compositions may be administered daily, for one or more times, for the effective treatment of acute or chronic conditions. One method of the present invention comprises administering at least one time a day a composition comprising maté constituent compounds. Methods also comprise administering such compositions more than one time per day, more than two times per day, more than three times per day and in a range from 1 to 15 times per day. Such administration may be continuously, as in every day for a period of days, weeks, months, or years, or may occur at specific times to treat or prevent specific conditions. For example, a person may be administered maté extract compositions at least once a day for years to treat obesity, or to enhance mental focus, cognition, and sense of well being, or to prevent cardiovascular disease or stroke.

The foregoing description includes the best presently contemplated mode of carrying out the present invention. This description is made for the purpose of illustrating the general principles of the inventions and should not be taken in a limiting sense. This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

All terms used herein are considered to be interpreted in their normally accepted usage by those skilled in the art. Patent and patent applications or references cited herein are all incorporated by reference in their entireties.

REFERENCES CITED

1. Gosman G, Guillame D, Taketa A T, and Schenkel E P: Triterpenoid saponins from Ilex paraguarensis. J Nat Prod 58:438-441, 1995.
2. Filip R, Lotito S B, Ferraro G and Fraga C G: Antioxidant activity of Ilex paraguareniensis and related species. Nutr Res 20:1437-1446, 2000.
3. Gosman G and Schenkel E P. A new saponin from maté, Ilex paraguariensis. J Nat Prod 52:1367-1370, 1989.
4. Saldana M D, Mahamed R S, Baer M G and Mazzafera P. Extraction of purine alkaloids from mate (Ilex paraguariensis) using supercritical $CO_2$. J Agric Food Chem 47:3804-3808, 1999.
5. Goldenberg D, Golz A and Joachims H Z. The beverage maté: a risk factor for cancer of the head and neck. Head Neck 25:595-601, 2003.
6. Gorzalczany S, Filip R, Alonso M R, et al. Choleretic effect and intestinal propulsion of "mate" (Ilex paraguariensis) and its substitutes or adulterants. J Ethnopharmacol 75:291-294, 2001.
7. Saldana M D, Zetzi C, Mohamed R S and Brunner G. Extraction of methylxanthines from guarana seeds, mate leaves, and cocoa beans using supercritical carbon dioxide and ethanol. J Agric Food Chem 50:4820-4826, 2002.
8. Graham H N. Mate. In Caffeine (Spiller G A, Ed.), CRC Press, Boca Raton, pp. 193-197, 1998.
9. Filip R, Lopez P, Gilberti G, et al. Phenolic compounds in seven South American Ilex species. Filoterapia 72:774-778, 2001.
10. Carini M, Facino R M, Aldini G, et al. Characterization of phenolic antioxidants from mate (Ilex paraguariensis) by liquid chromatography mass spectrometry and liquid chromatography/tandem mass spectrometry. Rapid Comm Mass Spect 12:1813-1819, 1998.
11. Schenkel E P, Montanha J A and Gosmann G. Triterpene saponins from mate, Ilex paraguariensis. Plenum Press, New York, 1996.
12. Vassallo A, Correa P, De Stephani E, et al. Esophageal cancer in Uruguay: a case-control study. J Natl Cancer Inst 75:1005-1009, 1985.
13. Gugliucci A and Stahl A F. Low density lipoprotein oxidation is inhibited by extracts of Ilex paraguariensis. Biochem Mol Biol Int 35:47-56, 1995.
14. Schinella G R, Troiani G, Davila V, et al. Antioxidant effects of an aqueous extract of Ilex paraguariensis. Biochem Biophys Res Commun 269:357-360, 2000.
15. Gugliucci A and Menini T. Comparative study on the antioxidant capacity of wines and other plant-derived beverages. Ann N Y Acad Sci 957:279-283, 2002.
16. Baisch A L M, Johnston K B and Stein F L P. Endothelium-dependent vasorelaxing activity of acqueous extracts of Ilex paraguariensis on mesenteric arterial bed of rats. J Ethnopharm 60:133-139, 1998.
17. De Stefani E, Fierro L, Correa P, et al. Mate drinking and risk of lung cancer in males: a case-control study from Uruguay. Cancer Epidemiol Biomarkers Prev 5:515-519, 1996.
18. De Stafani E, Correa P, Fierro L, et al. Black tobacco, mate, and bladder cancer. A case-control study from Uruguay. Cancer 67:536-540, 1991.
19. Pintos J, Franco E L, Oliveira B V, et al. Mate, coffee, and tea consumption and risk of cancers of the upper aerodigestive tract in southern Brazil. Epidemiology 5:583-590, 1994.

EXAMPLES

Example 1

The following ingredients are mixed for the formulation:

| | |
|---|---|
| Extract of I. paraguariensis | 150.0 mg |
| Stevioside (Extract of Stevia) | 12.5 mg |
| Carboxymethylcellulose | 35.5 mg |
| Lactose | 77.0 mg |
| Total | 275.0 mg |

The extract of I. paraguariensis comprises a ratio of theobromine to caffeine by weight of greater than 1.0. The caffeoyl content of the extract of I. paraguariensis by weight is greater than that found in the native maté plant material or conventional extract. The tannin content of the I. paraguariensis extract is reduced by greater than 80% by weight compared to that found in the respective native plant source or conventional extracts of the native plant source. The formulations can be made into any oral dosage form and administered daily or up to 15 times per day as needed for the physiological effect (weight reduction, enhancement of mental focus, cognition, physical/mental energy, and sense of well-being, relief from nervous depression, relaxant, anti-oxidant activity, diuresis, vasodilation, reduction of blood pressure, bronchial relaxation, asthma, COPD, arthritis/rheumatoid conditions, anti-inflammatory, glycation protection, HIV, and cancer).

Example 2

The following ingredients were mixed for the following formulation:

| | |
|---|---|
| Extract of I. paraguariensis | 90.0 mg |
| Theobromine (52%) | 3.4 mg |
| Caffeine (44%) | 2.9 mg |
| Theophylline (4%) | 0.3 mg |
| Vitamin C | 15.0 mg |
| Sucralose | 35.0 mg |
| Mung Bean Powder 10:1 | 50.0 mg |
| Mocha Flavor | 40.0 mg |
| Chocolate Flavor (RT#NV-24,397) | 20.0 mg |
| Total | 250.0 mg |

The percentages refer to the methylxanthines in the *I. paraguariensis* extract, respectively. The caffeoyl content of the maté extract (17.6 mg) is increased greater than 20% by weight compared to the respective natural plant source. The tannin content of the *I. paraguariensis* extract (1.4 mg) is reduced greater than 80% by weight compared to the respective native plant source. The formulation can be made into any dosage form and administered daily up to 15 times per day as needed for the physiological effect (weight reduction, enhancement of mental focus, cognition, physical/mental energy, and sense of well-being, relief from nervous depression, antioxidant activity, diuresis, vasodilation, anti-hypertension, bronchial relaxation, asthma, COPD, arthritis/rheumatoid conditions, anti-inflammatory, glycation protection, hepatic disorders, HIV, and cancer). This formulation has been used successfully to provide the beneficial effects with any deleterious secondary effects having been observed.

Example 3

The following ingredients were mixed for the following formulation:

| | |
|---|---|
| Extract of *I. paraguariensis* | 90.0 mg |
| Theobromine | 50.0 mg |
| Caffeine | 10.0 mg |
| Theophylline | 1.0 mg |
| Vitamin C | 15.0 mg |
| Sucralose | 40.0 mg |
| Mung Bean Powder 10:1 | 30.0 mg |
| Mocha Flavor Ungerer FK4578 | 60.0 mg |
| Bitterness Blocker | 3.0 mg |
| X-base M-500 | 50.0 mg |
| X-base Xanthan Gum | 1.0 mg |
| Total | 350.0 mg |

The extract of *I. paraguariensis* comprises theobromine in an amount that is greater by weight than caffeine. The caffeoyl content of the *I. paraguariensis* extract is enhanced 20% by weight greater than that found in the natural plant source material. The tannin content of the *I. paraguariensis* has been reduced by greater than 80% by weight compared to the natural plant source. Although this formulation has been made as a freeze dried rapid dissolve tablet, the formulation can be made into any oral dosage form and administered up to 15 times per day as needed for the physiological effect (weight reduction, enhancement of cognition, mental focus, physical/mental energy, and sense of well-being, reduction of nervous depression, antioxidant, diuresis, vasorelaxation, anti-hypertension, bronchial dilation, asthma, COPD, arthritis/rheumatoid conditions, anti-inflammatory, glycation protection, hepatic disorders, HIV, and cancer). This formulation has been used successfully in numerous trials to provide the beneficial effects without any deleterious secondary effects have been observed.

What is claimed is:

1. A method for making a maté extract composition having at least one predetermined characteristic, comprising, extracting native maté plant material using supercritical $CO_2$ conditions to obtain a mate extract composition, wherein the supercritical $CO_2$ conditions comprise a pressure of between about 7,250 and about 10,150 psi; and wherein the caffeine concentration is less than or equal to the theobromine concentration in the maté extract composition, and wherein at least one predetermined characteristic comprises a reduction in the tannin concentration when compared to tannin concentration of native maté plant material.

2. The method of claim 1, wherein at least one predetermined characteristic comprises a caffeoyl concentration that is greater than or equal to that of native maté plant material.

3. The method of claim 1, wherein the supercritical $CO_2$ conditions comprise an operating temperature between about 45° C. and about 100° C.

4. The method of claim 1, wherein ethanol is used as a cosolvent.

5. The method of claim 4, wherein the supercritical $CO_2$ conditions comprise an operating temperature between about 45° C. and about 100° C.

6. The method of claim 1, further comprising extracting the native maté plant material with a solution comprising water or a hydroalcoholic solution before extracting the native maté material using the supercritical $CO_2$ conditions.

7. The method of claim 1, wherein water is used as a cosolvent.

8. The method of claim 1, further comprising extracting the maté extract composition with a solution comprising water or a hydroalcoholic solution.

9. A method for making a maté extract composition having at least one predetermined characteristic, comprising, extracting native maté plant material using supercritical $CO_2$ conditions to obtain a mate extract composition, wherein the supercritical $CO_2$ conditions comprise a pressure of between about 9,000 psi and 10,000 psi, and wherein at least one predetermined characteristic is a reduction in the tannin concentration when compared to tannin concentration of native maté plant material.

10. The method of claim 9, wherein at least one predetermined characteristic comprises a reduction in the caffeine concentration compared to caffeine concentration of native plant material, or a caffeoyl concentration that is greater than or equal to that of native maté plant material.

11. The method of claim 10, wherein the caffeine concentration is less than or equal to the theobromine concentration in the mate extract composition.

12. The method of claim 9, wherein the supercritical $CO_2$ conditions comprise an operating temperature between about 45° C. and about 100° C.

13. The method of claim 9, wherein ethanol is used as a cosolvent.

14. The method of claim 9, wherein water is used as a cosolvent.

15. The method of claim 9, further comprising extracting the native maté plant material with a solution comprising water or a hydroalcoholic solution before extracting the native maté material using the supercritical $CO_2$ conditions.

16. The method of claim 9, further comprising extracting the maté extract composition with a solution comprising water or a hydroalcoholic solution.

17. A method for making a maté extract composition having at least one predetermined characteristic, comprising, extracting native maté plant material using supercritical $CO_2$ conditions to obtain a mate extract composition comprising at least one predetermined characteristic, wherein the supercritical $CO_2$ conditions comprise a pressure of about 9,000 psi, and wherein the temperature is about 55° C.

18. The method of claim 17, wherein at least one predetermined characteristic comprises a reduction in the caffeine concentration compared to caffeine concentration of native plant material, a reduction in the tannin concentration when compared to tannin concentration of native maté plant material, or a caffeoyl concentration that is greater than or equal to that of native maté plant material.

19. The method of claim 18, wherein the caffeine concentration is less than or equal to the theobromine concentration.

20. The method of claim 17, further comprising extracting the native maté plant material with a solution comprising water or a hydroalcoholic solution, before using the supercritical $CO_2$ conditions.

21. The method of claim 17, further comprising extracting the maté extract composition with a solution comprising water or a hydroalcoholic solution.

22. The method of claim 17, wherein ethanol or water is used as a cosolvent.

23. A method for making a maté extract composition having at least one predetermined characteristic, comprising, extracting native maté plant material using supercritical $CO_2$ conditions to obtain a mate extract composition, wherein the supercritical $CO_2$ conditions comprise a pressure of between about 7,250 and about 10,150 psi; wherein the caffeine concentration is less than or equal to the theobromine concentration in the maté extract composition, and wherein at least one predetermined characteristic comprises a caffeoyl concentration that is greater than or equal to that of native maté plant material.

24. The method of claim 23, further comprising at least one predetermined characteristic comprising a reduction in the tannin concentration when compared to tannin concentration of native maté plant material.

* * * * *